US00PP37167P2

(12) United States Plant Patent
Capo

(10) Patent No.: US PP37,167 P2
(45) Date of Patent: Dec. 23, 2025

(54) ***PETUNIA* PLANT NAMED 'KLEPH24734'**

(50) Latin Name: ***Petunia* x *atkinsiana (syn. P.* x *hybrida)***
Varietal Denomination: KLEPH24734

(71) Applicant: KLEMM + SOHN GMBH & CO. KG, Stuttgart (DE)

(72) Inventor: Antonella Capo, Latina (IT)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/260,362

(22) Filed: Jul. 4, 2025

(51) Int. Cl.
*A01H 5/02* (2018.01)
*A01H 6/82* (2018.01)

(52) U.S. Cl.
USPC ..... Plt./356.2
CPC ..... *A01H 6/824* (2018.05)

(58) Field of Classification Search
USPC ..... Plt./356.2
CPC ..... A01H 5/02
See application file for complete search history.

*Primary Examiner* — Kent L Bell
(74) *Attorney, Agent, or Firm* — Weatherly IP Solutions, LLC; James M. Weatherly

(57) ABSTRACT

A new *Petunia* plant particularly distinguished by large light violet flowers with darker violet veins and a semi-trailing plant habit, is disclosed.

1 Drawing Sheet

Genus and species: *Petunia* x *atkinsiana* (*syn. P.* x *hybrida*).

Variety denomination: 'KLEPH24734'.

BACKGROUND OF THE NEW PLANT

The present invention comprises a new and distinct variety of *Petunia,* botanically known as *Petunia* x *atkinsiana* (*syn. P.* x *hybrida*) and hereinafter referred to by the variety name 'KLEPH24734'. 'KLEPH24734' is a selection from a controlled cross between the proprietary female *Petunia* line *Petunia* 'KLEPH14245' (U.S. Plant Pat. No. 27,045) and the male *Petunia* line 'PH-2018-4744' (unpatented).

In July of 2019, the proprietary female *Petunia* line 'KLEPH14245' and the proprietary male *Petunia* line 'PH-2018-4744' were cross pollinated in Latina, Italy and seeds were obtained. The seeds were sown and plants were grown for evaluation. A plant line was selected in April 2020 in Latina, Italy and named 'KLEPH24734'. In May 2020, 'KLEPH24734' was first vegetatively propagated by terminal tip cuttings and tissue culture in Latina, Italy. 'KLEPH24734' was found to reproduce true to type in successive generations of asexual propagation via tissue culture and terminal tip cuttings.

SUMMARY

The following are the most outstanding and distinguishing characteristics of this new variety when grown under normal horticultural practices in Latina, Italy.

1. Large light violet flowers with darker violet veins; and
2. Semi-trailing plant habit.

DESCRIPTION OF THE PHOTOGRAPH

This new *Petunia* plant is illustrated by the accompanying photograph, which shows a close-up of the flowers of the plant.

The plant is about ten weeks old grown in Stuttgart, Germany in May 2022. The colors shown are as true as can be reasonably obtained by conventional photographic procedures.

DESCRIPTION OF THE NEW VARIETY

The following detailed descriptions set forth the distinctive characteristics of 'KLEPH24734'. The data which define these characteristics were collected from asexual reproductions carried out in Latina, Italy. Data was collected on thirteen-week-old plants grown indoors in Latina, Italy under greenhouse conditions in May 2025. Color references are to The R.H.S. Colour Chart of The Royal Horticultural Society of London (R.H.S.), 5$^{th}$ edition (2007).

Classification:

*Family.*—Solanaceae.
*Species.*—*Petunia* x *atkinsiana* (*syn. P.* x *hybrida*).
*Common name.*—*Petunia.*
*Variety.*—'KLEPH24734'.

Parentage:

*Female parent.*—*Petunia* 'KLEPH14245' (U.S. Plant Pat. No. 27,045).
*Male parent.*—*Petunia* 'PH-2018-4744' (unpatented).

Plant:

*Form and habit.*—High vigor, semi-trailing habit.
*Height* (*from top of soil*).—20.0 cm.
*Width* (*horizontal plant diameter*).—65.0 cm.
*Propagation type.*—Vegetative by terminal tip cuttings and tissue culture.
*Time to produce a finished flowering plant.*—About 12 weeks in winter under short day conditions, about 7 weeks in spring.
*Time to initiate and develop roots.*—2 to 3 weeks.
*Root description.*—Moderate density, moderate branching, white roots (RHS 155C).

Stems:

*Average number (basal).*—5.

*Length of basal branches (from the base of the stem to the tip).*—40.0 cm.

*Internode length.*—1.6 cm to 2.3 cm.

*Diameter of branches (from midpoint).*—0.3 cm.

*Stem color.*—RHS 138A.

*Anthocyanin.*—Absent.

*Texture.*—Pubescent.

Leaves:

*Arrangement.*—Alternate along the stem and opposite under the inflorescence.

*Length.*—5.5 cm.

*Width.*—3.0 cm to 4.5 cm.

*Shape.*—Elliptic to Obovate.

*Apex.*—Obtuse.

*Base.*—Attenuate.

*Margin.*—Entire.

*Immature leaf color.*—Upper surface: RHS 137C. Lower surface: RHS 138B.

*Mature leaf color.*—Upper surface: RHS N137B. Lower surface: RHS 138B.

*Texture.*—Upper surface: Pubescent. Lower surface: Pubescent.

*Venation pattern.*—Arcuate.

*Venation color.*—Upper surface: RHS N137B. Lower surface: RHS 138B.

*Petioles.*—Length: 3.0 cm. Diameter: 0.4 cm. Color: RHS 144B. Texture: Pubescent.

Flower bud:

*Shape.*—Irregularly oblong.

*Length.*—4.5 cm.

*Diameter.*—0.7 cm.

*Color at tight bud.*—RHS 84D.

*Texture.*—Pubescent.

Inflorescence:

*Blooming habit (flowering season).*—Continuously flowering during spring and summertime.

*Inflorescence type.*—Sympodial, with monochasial growth.

*Number of flowers per node.*—1.

*Lastingness of individual blooms on the plant.*—About 10 days.

*Fragrance.*—Absent.

*Flowers.*—Arrangement: Composed of 5 petals, fused at the base. Diameter (flower face): 7.3 cm. Depth (total length of flower): 6.5 cm. Throat/Funnel: Length: 3.3 cm. Diameter (at opening): 1.3 cm. Texture: Inner surface: Smooth. Outer surface: Pubescent. Color: Inner surface: RHS N92C. Outer surface: RHS N77C. Petals: Color, mature flower (fully opened): Upper surface: RHS 91C and RHS N88C at transition of corolla. tube with RHS N88A veins. Lower surface: RHS 85C. Apex: Cuspidate. Base: Fused. Shape: Funnelform. Margin: Entire. Strength of waviness: Medium. Degree of lobation: Medium.

*Calyx arrangement.*—5 sepals fused at the base.

*Sepals.*—Color: Upper surface: RHS 137A. Lower surface: RHS 137C. Length: 1.3 cm. Width: 0.4 cm. Shape: Oblanceolate. Apex: Rounded. Base: Attenuate. Margin: Entire. Texture: Upper surface: Pubescent. Lower surface: Pubescent.

*Pedicels.*—Color: RHS 144A. Length: About 2.0 cm. Diameter: 0.15 cm. Texture: Pubescent.

Reproductive organs:

*Stamens.*—Quantity: 5. Shape: Needle with oblong head. Filament: Length: From 1.2 cm to 1.6 cm. Diameter: 0.01 cm. Color: RHS 192C. Anther: Shape: Oblong. Color: RHS 91A. Length: 0.2 cm. Diameter: 0.15 cm. Pollen: Color: RHS 96B. Amount: Sparse.

*Pistils.*—Quantity per flower: 1. Length: 2.7 cm. Stigma color: RHS 139A. Style color: RHS 145B.

Fruit and seed set: None observed.

Disease and pest/insect resistance: None observed.

COMPARISON WITH PARENTAL LINES AND KNOWN VARIETY

'KLEPH24734' is a distinct variety of *Petunia*. 'KLEPH24734' is distinguished from its parents as described in Table 1:

TABLE 1

Comparison with Parental Lines

| Characteristic | Subject Variety 'KLEPH24734' | Female parent 'KLEPH14245' | Male Parent 'PH-2018'4744' |
|---|---|---|---|
| Flower color | Light violet with darker violet veins | Solid violet with cream colored throat | Solid dark pink violet |

'KLEPH24734' is most similar to the commercial *Petunia* plant named Surfinia Blue Vein 'Sunsolos' (unpatented). Differences between the two varieties are described in Table 2:

TABLE 2

Comparison with Similar Variety

| Characteristic | Subject Variety 'KLEPH24734' | Commercial line Surfinia Blue Vein 'Sunsolos' |
|---|---|---|
| Flower size | Big flowers | Smaller flowers |
| Earliness | Up to two weeks earlier than Surfinia Blue Vein 'Sunsolos' | Up to two weeks later than 'KLEPH24734' |

I claim:

1. A new and distinct variety of *Petunia* plant named 'KLEPH24734' as shown and described herein.

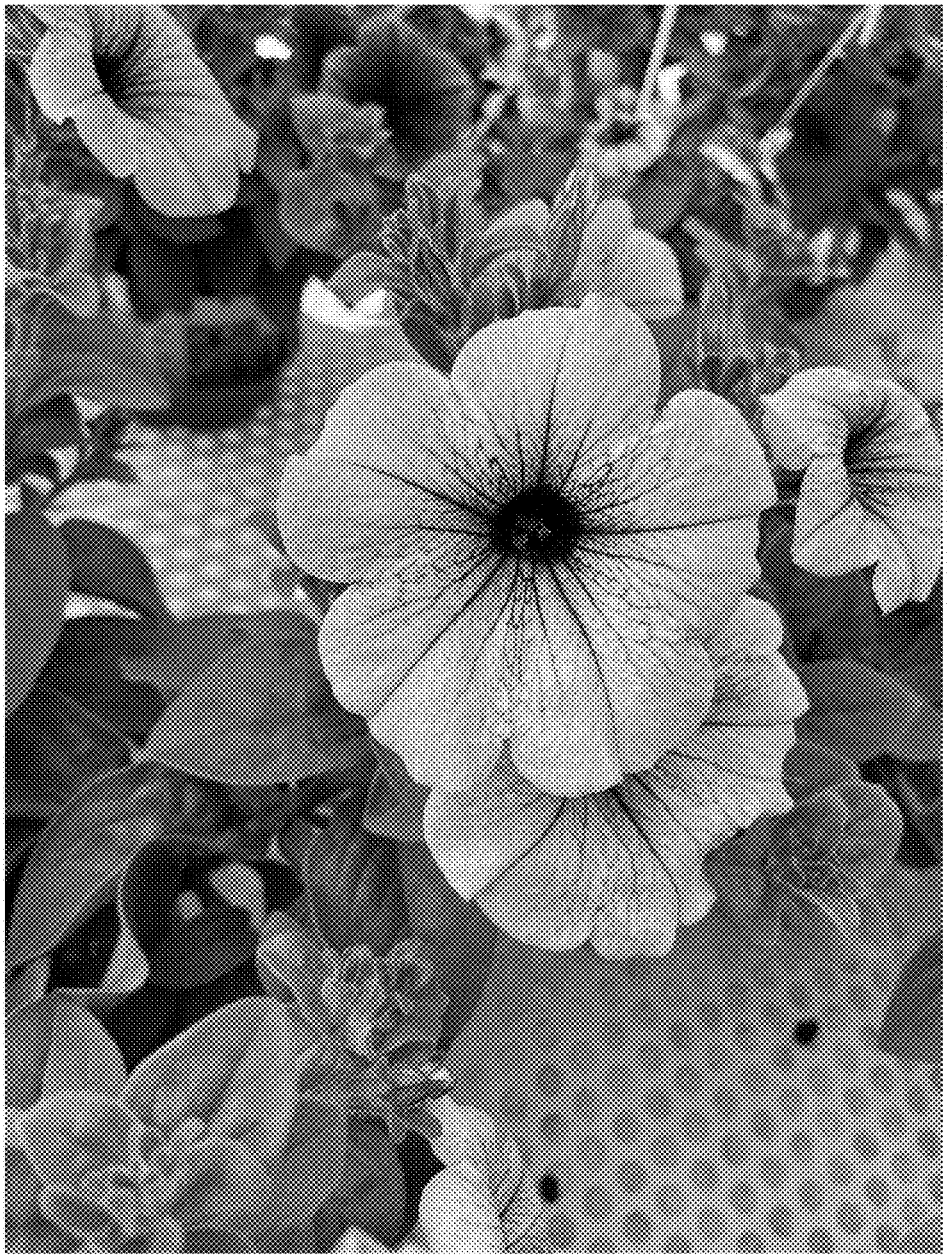

* * * * *